US010590062B1

(12) United States Patent
Chakraborty et al.

(10) Patent No.: US 10,590,062 B1
(45) Date of Patent: Mar. 17, 2020

(54) IRON-CATALYZED SELECTIVE PRODUCTION OF METHYL ESTERS FROM ALDEHYDES

(71) Applicant: Eastman Chemical Company, Kingsport, TN (US)

(72) Inventors: Sumit Chakraborty, Johnson City, TN (US); Steven J. Adams, Gray, TN (US); Robert Thomas Hembre, Johnson City, TN (US); Leslie Sharon Depew, Kingsport, TN (US)

(73) Assignee: Eastman Chemical Company, Kingsport, TN (US)

( * ) Notice: Subject to any disclaimer, the term of this patent is extended or adjusted under 35 U.S.C. 154(b) by 0 days.

(21) Appl. No.: 16/188,976

(22) Filed: Nov. 13, 2018

(51) Int. Cl.
*C07C 67/39* (2006.01)
*C07C 67/44* (2006.01)
*B01J 31/22* (2006.01)
*C07C 69/003* (2006.01)
*C07C 69/013* (2006.01)

(52) U.S. Cl.
CPC .......... *C07C 67/39* (2013.01); *B01J 31/2295* (2013.01); *C07C 67/44* (2013.01); *B01J 2231/76* (2013.01); *B01J 2531/842* (2013.01); *B01J 2540/10* (2013.01); *C07C 69/003* (2013.01); *C07C 69/013* (2013.01)

(58) Field of Classification Search
CPC ......... C07C 67/39; C07C 67/40; C07C 67/44; C07C 67/297; B01J 31/2295; B01J 2231/76; B01J 2531/842; B01J 2540/10
See application file for complete search history.

(56) References Cited

U.S. PATENT DOCUMENTS

| 3,215,712 A | * | 11/1965 | Hubel | .................. | C07C 1/325 |
| | | | | | 552/294 |
| 5,892,102 A | * | 4/1999 | Mikami | ............... | B01J 23/6447 |
| | | | | | 502/170 |
| 2003/0176300 A1 | | 9/2003 | Kodali et al. | | |
| 2010/0317824 A1 | | 12/2010 | Thoen et al. | | |
| 2016/0137582 A1 | | 5/2016 | Frey et al. | | |
| 2016/0297741 A1 | | 10/2016 | Janka et al. | | |

FOREIGN PATENT DOCUMENTS

| JP | 08-099933 A | | 4/1996 | |
| JP | H11-43463 A | * | 2/1999 | ............. B01K 23/72 |
| JP | 2001-220367 A | | 8/2001 | |

OTHER PUBLICATIONS

JP H11-43463(a), Marutani, K. et al., Production of Carboxylic Ester, English translation, 6 pages (Year: 1999).*

Johnson, T. C., et al., (Cyclopentadienone)iron Shvo Complexes: Synthesis and Applications to Hydrogen Transfer Reactions, 2011, Organometallics, vol. 30, issue 7, pp. 1859-1868 (Year: 2011).*
Yang, Q., et al., New air-stable iron catalyst for efficient dynamic kinetic resolution of secondary benaylic and aliphatic alcohols, May 13, 2017, Tetrahedron Letters, vol. 58, pp. 2487-2489 (Year: 2017).*
Eberhardt, N.A., et al., Dehydrogenative Coupling of Aldehydes with alcohols catalyzed by a nickel hydride complex, Mar. 13, 2019, Organometallics, vol. 38, issue 7, pp. 1468-1478 (Year: 2019).*
Office Action dated Jun. 10, 2019 received in co-pending U.S. Appl. No. 16/188,930.
Co-pending U.S. Appl. No. 16/188,930, filed Nov. 13, 2018; Chakraborty et al.
Co-pending U.S. Appl. No. 16/188,958, filed Nov. 13, 2018; Chakraborty et al.
Blum et al.; "Catalytically Reactive Ruthenium Intermediates in the Homogeneous Oxidation of Alcohols to Esters;" Israel Journal of Chemistry; vol. 24; 1984; pp. 144-148.
Blum et al.; "Catalytically Reactive ($\eta^4$-tetracyclone)(CO)$_2$(H)$_2$Ru and Related Complexes in Dehydrogenation of Alcohols to Esters;" Journal of Organometallic Chemistry; 1985; 282; pp. C7-C10.
Blum et al.; "Structure of $\eta^4$-Ph$_4$C$_4$CO)(CO)$_3$Ru—a Catalyst Precursor in H-Transfer and Dehydrogenation Reactions of Alcohols;" Inorganica Chimica Acta; 1985; 97; pp. L25-L26.
Chakraborty et al.; "Well-Defined Iron Catalysts for the Acceptorless Reversible Dehydrogenation-Hydrogenation of Alcohols and Ketones;" ACS Catal.; 2014; 4; pp. 3994-4003.
Gianetti et al.; "Nitrous Oxide as a Hydrogen Acceptor for the Dehydrogenative Coupling of Alcohols;" Angew. Chem. Int. Ed.; 2016; 55; pp. 1854-1858.
Grigg et al.; "Oxidation of Alcohols by Transition Metal Complexes—IV;" Tetrahedron; 1981; vol. 37; No. 24; pp. 4313-4319.
Gunanathan et al.; "Applications of Acceptorless Dehydrogenation and Related Transformations in Chemical Synthesis;" Science; 2013; vol. 341; pp. 249.
Gunanathan et al.; "Direct Conversion of Alcohols to Acetals and H2 Catalyzed by an Acridine-Based Ruthenium Pincer Complex;" J. Am. Chem. Soc.; 2009; 131; pp. 3146-3147.
Karmel et al.; "Mono(imidazoline-2-iminato) Actinide Complexes: Synthesis and Application in the Catalytic Dimerization of Aldehydes;" J. Am. Chem. Soc.; 2014; 136; pp. 17180-17192.
Khusnutdinova et al.; "Metal-Ligand Cooperation;" Angew. Chem. Int. Ed.; 2015; 54; pp. 12236-12273.
Kiran et al.; "Single-Step Conversion of Electron-Deficient Aldehydes into the Corresponding Esters in Aqueous Alcohols in the Presence of Iodine and Sodium Nitrite;" Synthesis; 2010; 2; pp. 276-282.
Kuriyama et al.; "Catalytic Hydrogenation of Esters. Development of an Efficient Catalyst and Processes for Synthesising (R)-1,2-Propanediol and 2-(/-Menthoxy)ethanol;" Org. ProcessRes. Dev.; 2012; 16; pp. 166-171.

(Continued)

*Primary Examiner* — Yate' K Cutliff
(74) *Attorney, Agent, or Firm* — Matthew W. Smith

(57) ABSTRACT

A process for making methyl esters in high yields is provided. The process comprises contacting aliphatic or aromatic aldehydes and methanol with an iron catalyst, to catalyze the dehydrogenative coupling between aliphatic or aromatic aldehydes and methanol. The reaction is highly selective (<99.9%) toward the formation of methyl esters over homoesters and alcohols and operates at temperatures of less than 100° C. for 2-8 hours.

6 Claims, No Drawings

(56) References Cited

OTHER PUBLICATIONS

Lee et al.; "N-Heterocyclic Carbene Catalyzed Oxidative Macrolactonization: Total Synthesis of (+)-Dactylolide;" Angew. Chem. Int. Ed.; 2012; 51; pp. 5735-5738.

Murahashi et al.; "Ruthenium-Catalyzed Oxidative Transformation of Alcohols and Aldehydes to Esters and Lactones;" J. Org. Chem.; 1987; 52; pp. 4319-4327.

Murahasi et al.; "Ruthenium Catalyzed Transformation of Alcohols to Esters and Lactones;" Tetrahedron Letters; 1981; vol. 22; No. 52; pp. 5327-5330.

Nielsen et al.; "Towards a Green Process for Bulk-Scale Synthesis of Ethyl Acetate: Efficient Acceptorless Dehydrogenation of Ethanol;" Angew. Chem. Int. Ed.; 2012; 51; pp. 5711-5713.

Rueping et al.; "Asymmetric oxidative Lewis base catalysis—unifying iminium and enamine organocatalysis with oxidations;" Chem. Commun.; 2012; 48; pp. 2201-2203.

Sarkar et al.; "NHC Catalyzed Oxidations of Aldehydes to Esters: Chemoselective Acylation of Alcohols in Presence of Amines;" J. Am. Chem. Soc.; 2010; 132; pp. 1190-1191.

Spasyuk et al.; "Acceptorless Dehydrogenative Coupling of Ethanol and Hydrogenation of Esters and Imines;" Organometallics; 2012; 31; pp. 5239-5242.

Spasyuk et al.; "From Esters to Alcohols and Back with Ruthenium and Osmium Catalysts;" Angew. Chem. Int. Ed.; 2012; 51; pp. 2772-2775.

Spasyuk et al.; "Chemoselective Hydrogenation of Carbonyl Compounds and Acceptorless Dehydrogenative Coupling of Alcohols;" J. Am. Chem. Soc.; 2015; 137; pp. 3743-3746.

Srimani et al.; "Ruthenium Pincer-Catalyzed Cross-Dehydrogenative Coupling of Primary Alcohols with Secondary Alcohols under Neutral Conditions;" Adv. Synth. Catal.; 2012; 354; pp. 2403-2406.

Sumino et al.; "Carbonylation Reactions of Alkyl Iodides through the Interplay of Carbon Radicals and Pd Catalysts;" Acc. Chem. Res.; 2014; 47; pp. 1563-1574.

Toubiana et al.; "The true catalyst in hydrogen transfer reactions with alcohol donors in the presence of $RuCl_2(PPh_3)_3$ is ruthenium(0) nanoparticles;" Catal. Sci. Technol.; 2012; 2; pp. 1644-1653.

Trincado et al.; "Molecular catalysts for hydrogen production from alcohols;" Energy Environ. Sci.; 2014; 7; pp. 2464-2503.

Whittaker et al.; "Nickel-Catalyzed Dehydrogenative Cross-Coupling: Direct Transformation of Aldehydes into Esters and Amides;" Angew. Chem. Int. Ed.; 2015; 54; pp. 1312-1315.

Yang et al.; "Substitution of alcohols by N-nucleophiles via transition metal-catalyzed dehydrogenation;" Chem. Soc. Rev.; 2015; 44; pp. 2305-2329.

Zhang et al.; "Electron-Rich PNP- and PNN-Type Ruthenium(II) Hydrido Borohydride Pincer Complexes. Synthesis, Structure, and Catalytic Dehydrogenation of Alcohols and Hydrogenation of Esters;" Organometallics; 2011; 30; pp. 5716-5724.

Zhang et al.; "Facile Conversion of Alcohols into Esters and Dihydrogen Catalyzed by New Ruthenium Complexes;" J. Am. Chem. Soc.; 2005; 127; pp. 10840-10841.

Office Action dated Jul. 9, 2019 received in co-pending U.S. Appl. No. 16/188,958.

Office Action dated Nov. 13, 2019 received in co-pending U.S. Appl. No. 16/188,958.

Thermo Fisher Scientific product page for Acros organics 5.4M (30 wt%) solution in methanol, downloaded from https://www.fishersci.com/shop/products/sodium-methoxide-5-4m-30-wt-solution-methanol-acroseal-acros-organics-2/AC428361000 on Jul. 2, 2019 (Year: 2019).

* cited by examiner

IRON-CATALYZED SELECTIVE PRODUCTION OF METHYL ESTERS FROM ALDEHYDES

FIELD OF THE INVENTION

The invention generally relates to the field of organic chemistry. It particularly relates to the production of methyl esters from aldehydes using a novel iron-based catalyst.

BACKGROUND OF THE INVENTION

Esters are among the most important and abundant functional groups in chemistry and they are widely found in food, pharmaceutical, flavor, and fine and bulk chemical industries. There are classical methods, e.g. reaction with carboxylic acid derivatives, carbonylation and the Tischenko reaction, which could be used to prepare ester compounds. The coupling of aldehydes with alcohols and coupling of two alcohols in the presence of external oxidants can also form esters. An alternative approach is the dehydrogenative coupling of two alcohols or aldehydes with alcohols with the release of $H_2$.

Acceptorless dehydrogenative homo-coupling of alcohols have been reported however a need still exists for a catalytic process that allows for the chemoselective dehydrogenative cross-coupling of aldehydes with methanol to afford corresponding methyl esters in high yields and moderate selectivities.

The present invention addresses this need as well as others, which will become apparent from the following description and the appended claims.

SUMMARY OF THE INVENTION

The invention is as set forth in the appended claims.

In one embodiment the invention is a process for preparing esters comprising:
a) combining an aldehyde having the formula $R_1CO$ with an alcohol having the formula $R_2OH$ to form a first mixture;
b) heating the first mixture in the presence of an iron catalyst to form an ester having the formula $R_1COR_2O$ and $H_2$;
wherein $R_1$ is a $C_4$ to $C_8$ aliphatic, alicyclic or aromatic group and wherein $R_2$ is a $C_1$ to $C_4$ group.

In another embodiment the catalyst has the structure (1):

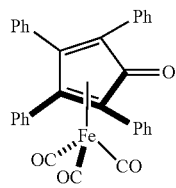

(1)

It has been surprisingly discovered that an iron catalyst mediates selective formation of methyl-2-ethylhexanoate via a reaction between 2-ethylhexenal (2-EHenal) and MeOH under mild conditions (<100° C.). We have also demonstrated that an equimolar mixture of 2-EHMe and 2-EH alcohol is produced when 2-HEH is used as the feedstock

DETAILED DESCRIPTION OF THE INVENTION

As used herein the following terms have the meaning as described below:
The term "M2EH" refers to methyl-2-ethylhexanoate.
The term "TEG" refers to triethylene glycol.
The term "TEG-2EH" refers to triethylene glycol 2-ethylhexanoate.
The term "2-HEH" refers to 2-ethylhexaldehyde.
The term "MeOH" refers to methanol.
The term "2-EHMe" refers to methyl 2-ethylhexanoate
The term "2EH" refers to 2-ethylhexyl alcohol.
The term "2EH2EH" refers to (2-ethylhexyl)2-ethylhexanoate.

As used herein, the indefinite articles "a" and "an" mean one or more, unless the context clearly suggests otherwise. Similarly, the singular form of nouns includes their plural form, and vice versa, unless the context clearly suggests otherwise While attempts have been made to be precise, the numerical values and ranges described herein should be considered approximations (even when not qualified by the term "about"). These values and ranges may vary from their stated numbers depending upon the desired properties sought to be obtained by the present invention as well as the variations resulting from the standard deviation found in the measuring techniques. Moreover, the ranges described herein are intended and specifically contemplated to include all sub-ranges and values within the stated ranges. For example, a range of 0 to 100 is intended to describe and include all values within the range including sub-ranges such as 0.1-99.9, 60 to 90 and 70 to 80.

We examined a reaction with 2-ethylhexaldehyde (2-HEH) and methanol (MeOH) (Table 1). In the absence of a catalyst, reacting 2-ethylhexaldehyde with excess of MeOH (5 equivalents) converted the aldehyde into a dimethyl acetal in MeOH at 90° C. No ester formation was observed under catalyst-free condition. Next, several homogeneous catalysts were screened to facilitate the formation of corresponding methyl ester (methyl 2-ethylhexanoate). These results are summarized in Table 1. Simple metal precursor complexes such as [Cp*RhCl$_2$]$_2$, [Cp*IrCl$_2$]$_2$, Ru$_3$(CO)$_{12}$ (Cp*=1,2,3,4,5-pentamethylcyclopentadiene) failed to produce any methyl 2-ethylhexanoate (entries 1-3) and only trace amounts of 2-ethylhexyl alcohol was produced in these reactions. Ruthenium and iridium-based homogeneous dehydrogenation catalysts, supported by pincer-type ligands, also showed negligible reactivity and selectivity toward forming 2-EHMe. For example, Milstein's (PNN)Ru(H)(CO)Cl catalyst in the presence of KOH afforded 2-EHMe and 2-ethylhexylalcohol (2-EH) with a relative ratio of 1:1.2 and the overall conversion of 2-HEH reached to 22% after 6 hours at 90° C. (entry 4). The homoester of 2-HEH aldehyde, (2-ethylhexyl)2-ethylhexanoate (2EH2EH), was also formed in a considerable amount (11%) during this reaction. In addition to Milstein's catalyst, Takasago's Ru-MACHO catalyst afforded 2-EH and 2EH2EH as major products and 2-EHMe was only produced in small quantities (entry 5).

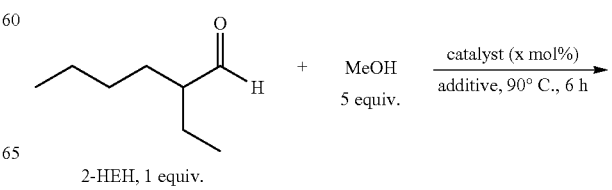

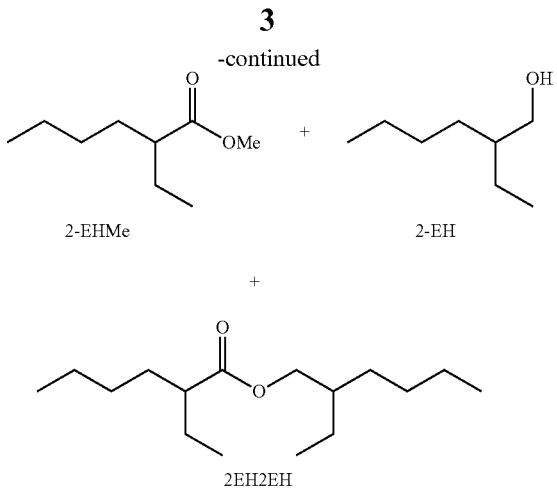

2-EHMe      2-EH

2EH2EH

TABLE 1

Catalyst Screening Studies for 2EH-MeOH Coupling Reaction.

| Entry | Catalyst (mol %) | Additives (mol %) | Yield of 2-EHMe (%) | Yield of 2-EH (%) | Yield of 2EH2EH (%) |
|---|---|---|---|---|---|
| 1[a] | [Cp*RhCl$_2$]$_2$ (0.5) | NaOAc(2) | 0 | 3.1 | 0 |
| 2[a] | [Cp*IrCl$_2$]$_2$ (0.5) | NaOAc(2) | 0 | 2.2 | 0 |
| 3[a] | Ru$_3$(CO)$_{12}$ (0.33) | — | 0 | 6.9 | 0 |
| 4 | (Ru pincer complex) | NaOMe(2) | 2.3 | 13.2 | 11.6 |
| 5 | (Ru PNP complex) | NaOMe(2) | 1.1 | 15.3 | 13.9 |

This invention can be further illustrated by the following examples of preferred embodiments thereof, although it will be understood that these examples are included merely for purposes of illustration and are not intended to limit the scope of the invention unless otherwise specifically indicated.

EXAMPLES

General Experimental Information

Unless otherwise noted, all the organometallic compounds were handled under a nitrogen atmosphere using standard Schlenk and glovebox techniques. Anhydrous methanol (99.7% grade), toluene, p-xylene, Aromatic 200 and mesitylene (98%) were purchased from commercial sources and stored with 4 Å molecular sieves. All aldehydes were purchased from commercial sources and freshly vacuum-distilled prior to use. Other commercially available catalysts were purchased from respective commercial sources and used without further purification. $^1$H NMR spectra were recorded on Bruker Avance-500 MHz spectrometers. Chemical shift values in $^1$H NMR spectra were referenced internally to the residual solvent resonances (b 7.16 for benzene-d$_6$). Iron catalyst was prepared using the literature procedure (Scheme 1).

Synthesis of Iron Catalyst (1), Scheme 3.

Under a nitrogen atmosphere, a 500 mL Schlenk flask, fitted with a condensor and stir bar, was charged with iron dodecacarbonyl, tetraphenyl cyclopentadienone, and 200 mL anhydrous toluene. The resulting mixture was heated to 80° C. for 20 hours, cooled to room temperature, and mixture was passed through silica gel column to elute the desired catalyst as orange-yellow liquid. Evaporation of the solvent afforded the product in 86% isolated yield.

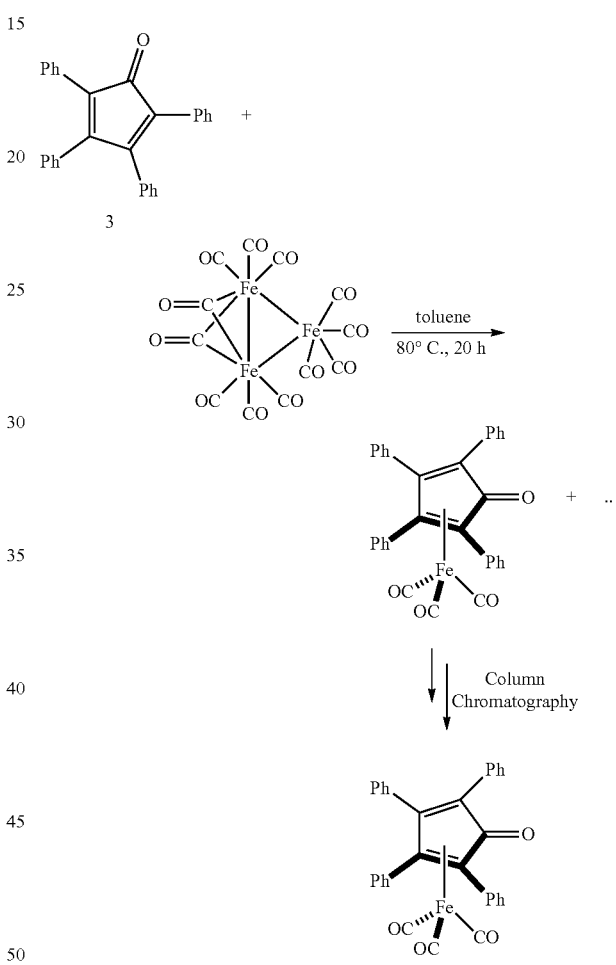

Synthesis of methyl 2-ethylhexanoate from 2-ethylhexaldehyde

Under a nitrogen atmosphere, an oven-dried 25 mL Schlenk tube equipped with a magnetic stir-bar and a Teflon plug was charged with the iron catalyst (1 mol %), 2-ethylhexaldehyde (2-HEH) (1.6 mL, 10 mmol), and anhydrous methanol (2 mL). The resulting mixture was heated at 90° C. for 3 hours using an oil-bath. After that the vessel was gradually allowed to come to room temperature and the volatiles (H$_2$, MeOH vapor) were carefully removed by opening the Teflon plug inside a hood. The liquid sample was analyzed by GC and GC-MS to determine the yield of methyl 2-ethylhexanoate and identify side-products.

Synthesis of methyl 2-ethylhexanoate from 2-EHenal

Under a nitrogen atmosphere, an oven-dried 100 mL Schlenk tube equipped with a magnetic stir-bar and a Teflon plug was charged with the iron catalyst (1 mol %), 2-ethyl-2-hexenal (2EHenal) (1.57 mL, 10 mmol), and anhydrous methanol (2 mL). The resulting mixture was heated at 90° C. for 3 hours using an oil-bath. After that the vessel was gradually allowed to come to room temperature and the volatiles ($H_2$, MeOH vapor) were carefully removed by opening the Teflon plug inside the hood. The liquid sample was analyzed by GC and GC-MS to determine the yield of methyl 2-ethylhexanoate (97.8 wt %) and identify other side-products

Synthesis of methyl benzoate from benzaldehyde

Under a nitrogen atmosphere, an oven-dried 100 mL Schlenk tube equipped with a magnetic stir-bar and a Teflon plug was charged with the iron catalyst (1.0 mol %), benzalaldehyde (1.35 g, 10 mmol, 99% purity), and anhydrous methanol (2 mL). The resulting mixture was heated at 90° C. for 3 hours using an oil-bath. After that the vessel was gradually allowed to come to room temperature and the volatiles ($H_2$, MeOH vapor) were carefully removed by opening the Teflon plug inside the hood. The liquid sample was analyzed by GC and GC-MS to determine the yield of methyl benzoate and identify other side products In summary, we have demonstrated that Shvo's catalyst catalyzes the dehydrogenative coupling between aliphatic or aromatic aldehydes and MeOH to afford corresponding methyl esters in high yields. The reaction is highly selective (up to <99.9%) toward the formation of methyl esters and operates under mild conditions (<100° C., 2-8 hours). The catalytic activity and the structure of the catalyst remain unchanged after several catalytic runs. An iron catalyst (1) shown below exhibited excellent reactivity and selectivity toward the formation of methyl esters from corresponding aldehydes via coupling with MeOH. When one equivalent of 2-EH was treated with five equivalents of MeOH at 90° C. in the presence of 1 mol % of ($\mu^4$-$Cp^{Me4}$)Fe(CO)$_3$ catalyst (1), a mixture containing 50:45 ratio of 2-EHMe and 2-EH were formed after 3 hours (Table 2, entry 1). No starting aldehyde remained after the reaction suggesting 100% aldehyde conversion. Traces of 2EH2EH, and unsaturated 2-EH methyl ester were also produced as byproducts in this reaction. The catalytic reaction could also be carried out in non-polar aromatic solvents such as toluene, p-xylene, mesitylene and Aromatic 200 without affecting the reactivity and selectivity.

TABLE 2

Iron-Catalyzed Synthesis of Methyl Esters from Aldehydes.[a]

| entry | substrate | product | time (h) | wt % yield |
|---|---|---|---|---|
| 1 | ![aldehyde] | ![ester-OMe] | 3 | 50.4 |
| 2 | ![unsaturated aldehyde] | ![ester-OMe] | 3 | 89.2 |
| 3 | ![benzaldehyde] | ![methyl benzoate] | 3 | 55.7 |

[a]Catalytic Conditions: [catalyst] = 0.025 (M), [aldehyde] = 2.5 (M), MeOH = 25 mmol, 1 mL, neat conditions, stir speed = 350 rpm, 90° C. (oil-bath temperature).

We have demonstrated that the iron catalyst (1) catalyzes dehydrogenative coupling between aliphatic or aromatic aldehydes and MeOH to afford corresponding methyl esters in moderate to high yields. The reaction is chemoselective toward the formation of methyl esters when substrate containing internal C=C bond is employed and the reaction operates under mild conditions (<100° C., 2-8 hours). Experiments show that the catalytic activity and the structure of the catalyst (1) remain unchanged after two catalytic runs.

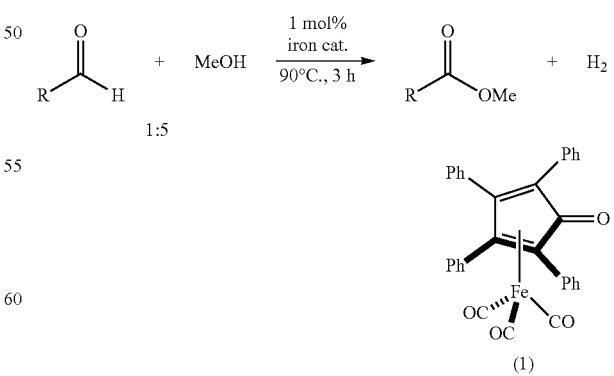

Remarkably, the coupling reaction between 2-EHenal and MeOH produced the saturated methyl 2-ethylhexanoate in 89.2% yield (Table 2, entry 2). The rest of the material accounts for unreacted 2EHenal, 2EH2EH, unsaturated esters, and 2-EH. This result indicates that the $H_2$ gas produced during the first 2EHenal-methanol coupling step is utilized to hydrogenate the C=C double bonds in the presence of the iron catalyst. This direct coupling of 2EHenal with methanol is an important discovery because it eliminates the reaction step for producing 2-HEH from 2-EHenal by hydrogenation with a heterogeneous catalyst (Scheme 1). In addition to aliphatic substrates, aromatic aldehydes such as benzaldehyde also afforded corresponding methyl esters in ~56% yield. This reaction could be used for dimethyl terephthalate (DMT) synthesis using terephthaldehyde as the reagent.

In the specification, there have been disclosed certain embodiments of the invention and, although specific terms are employed, they are used in a generic and descriptive sense only and not for purposes of limitation, the scope of the invention being set forth in the following claims.

We claim:

1. A process for preparing esters comprising:
   a) combining an aldehyde having the formula $R_1CO$ with an alcohol having the formula $R_2OH$ and an iron catalyst to form a first mixture;
   b) heating the first mixture to form an ester having the formula $R_1COR_2O$ and $H_2$;

wherein $R_1$ is a $C_4$ to $C_8$ aliphatic, alicyclic or aromatic group and wherein $R_2$ is a $C_1$ to $C_4$ group, and wherein said iron catalyst is represented by the structure:

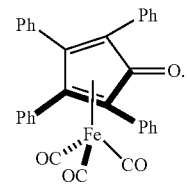

2. The process of claim 1 wherein $R_2OH$ is selected from the group consisting of methanol, ethanol, propanol, isopropanol, butanol, isobutanol and ethylene glycol.

3. The process of claim 1 wherein $R_2OH$ is methanol.

4. The process of claim 1 wherein step b) is conducted at a temperature of less than 100° C. for about 2 hours to about 8 hours.

5. The process of claim 1 wherein the molar ratio of $R_1CO$ to $R_2OH$ in said first mixture is from 1:1 to 1:5.

6. The process of claim 1 wherein the molar amount of catalyst in said first mixture is from about 0.25 mole percent to about 1 mole percent.

* * * * *